(12) United States Patent
Laidler et al.

(10) Patent No.: US 9,657,061 B2
(45) Date of Patent: May 23, 2017

(54) HYDROCHLORIDE SALT OF PEPTIDE AND ITS USE IN COMBINATION WITH OTHER PEPTIDES FOR IMMUNOTHERAPY

(71) Applicant: Circassia Limited, Oxford (GB)

(72) Inventors: Paul Laidler, Oxford (GB); Imre Farkas, Bubendorf (CH)

(73) Assignee: Circassia Limited, Oxford (GB)

( * ) Notice: Subject to any disclaimer, the term of this patent is extended or adjusted under 35 U.S.C. 154(b) by 0 days.

(21) Appl. No.: 14/400,052

(22) PCT Filed: May 9, 2013

(86) PCT No.: PCT/GB2013/051201
§ 371 (c)(1),
(2) Date: Nov. 10, 2014

(87) PCT Pub. No.: WO2013/167897
PCT Pub. Date: Nov. 14, 2013

(65) Prior Publication Data
US 2015/0110820 A1    Apr. 23, 2015

(30) Foreign Application Priority Data

May 11, 2012 (GB) .................................. 1208293.9

(51) Int. Cl.
*C07K 7/08* (2006.01)
*A61K 39/35* (2006.01)
*A61K 45/06* (2006.01)
*A61K 39/00* (2006.01)

(52) U.S. Cl.
CPC ............... *C07K 7/08* (2013.01); *A61K 39/35* (2013.01); *A61K 45/06* (2013.01); *A61K 2039/577* (2013.01)

(58) Field of Classification Search
CPC ..................................................... C07K 7/08
USPC ....................................................... 530/327
See application file for complete search history.

(56) References Cited

FOREIGN PATENT DOCUMENTS

| GB | 2455108 | * | 6/2009 |
|---|---|---|---|
| WO | WO-03/047618 A2 | | 6/2003 |
| WO | WO-2007/084460 A2 | | 7/2007 |
| WO | WO-2008/145998 A1 | | 12/2008 |
| WO | WO-2008/146003 A1 | | 12/2008 |
| WO | WO-2009/022155 A2 | | 2/2009 |
| WO | WO-2010/061193 A2 | | 6/2010 |

OTHER PUBLICATIONS

Worm, Margitta (Journal of Allergy and Clinical Immunology 127(1), 89-97, 2011).*
Bastin, Organic Process Research & Development 4, 427-435, 2000.*
Hay, Making peptides. *Manufacturing chemist: incorporating Chemical age.* HPCi Media, 2012 (6 pages).
Avanti, "Innovative Strategies for Stabilization of Therapeutic Peptides in Aqueous Formulations," <https://www.tipharma.com/fileadmin/user_upload/Theses/PDF/Christina_Avanti_D6-202.pdf>. Thesis, University of Groningen, Jul. 2, 2012 (149 pages).
Beck et al., "Peptides as tools and drugs for immunotherapies," J Pept Sci. 13(9):588-602 (2007).
Roux et al., "Elimination and exchange of trifluoroacetate counter-ion from cationic peptides: a critical evaluation of different approaches," J Pept Sci. 14(3):354-9 (2008).
Vergote et al., "Quality specifications for peptide drugs: a regulatory-pharmaceutical approach," J Pept Sci. 15(11):697-710 (2009).
International Search Report and Written Opinion for International Patent Application No. PCT/GB2013/051201, dated Jul. 31, 2013 (10 pages).
Andrushchenko et al., "Optimization of the hydrochloric acid concentration used for trifluoroacetate removal from synthetic peptides," J Pept Sci. 13(1):37-43 (2007).
Cleland et al., "Formulation and delivery of proteins and peptides: design and development strategies," ACS Symposium Series. Chapter 1:1-19 (1994).
Helm et al., "Stability of gonadorelin and triptorelin in aqueous solution," Pharm Res. 7(12):1253-6 (1990).

* cited by examiner

*Primary Examiner* — David Lukton
(74) *Attorney, Agent, or Firm* — Clark & Elbing LLP; Susan M. Michaud

(57) ABSTRACT

The present invention relates to a hydrochloride salt of a peptide consisting of the sequence of CPAVKRDVDLFLT (SEQ ID NO: 1) as well as its combinations with other peptides for immunosuppressive purposes.

1 Claim, 4 Drawing Sheets

Fig. 2

|  | $b_1$ | $b_2$ | $b_3$ | $b_4$ | $b_5$ | $b_6$ | $b_7$ | $b_8$ | $b_9$ | $b_{10}$ | $b_{11}$ | $b_{12}$ |
|---|---|---|---|---|---|---|---|---|---|---|---|---|
| m/z expected | 104.0 | 201.1 | 272.1 | 371.2 | 499.3 | 655.4 | 770.4 | 869.5 | 984.5 | 1097.6 | 1244.6 | 1357.7 |
| m/z observed | n.o. | 201.1 | 272.2 | 371.3 | n.o. | n.o. | 770.5*[1] | 869.5*[1] | 984.5[1] | 1097.7[1] | 1244.8[1] | 1357.9[1] |
|  | H-Cys- | Pro- | Ala- | Val- | Lys- | Arg- | Asp- | Val- | Asp- | Leu- | Phe- | Leu- | Thr-OH |
| m/z expected | | 1373.8 | 1276.7 | 1205.7 | 1106.6 | 978.5 | 822.4 | 707.4 | 608.3 | 493.3 | 380.2 | 233.2 | 120.1 |
| m/z observed | | 687.5*[2] | 1276.9* | 1205.8* | 1106.7* | 978.5* | n.o. | n.o. | n.o. | n.o. | 380.3* | 233.2 | 120.1 |
|  | | $y_{12}''$ | $y_{11}''$ | $y_{10}''$ | $y_9''$ | $y_8''$ | $y_7''$ | $y_6''$ | $y_5''$ | $y_4''$ | $y_3''$ | $y_2''$ | $y_1''$ |

Notes:
n.o. = Not Observed.
* = Weak Signal.
[1] = Also Observed as Doubly Charged.
[2] = Doubly Charged Ion.

Fig. 4

| | $b_1$ | $b_2$ | $b_3$ | $b_4$ | $b_5$ | $b_6$ | $b_7$ | $b_8$ | $b_9$ |
|---|---|---|---|---|---|---|---|---|---|
| m/z expected | 104.0 | 201.1 | 272.1 | 371.2 | 499.3 | 655.4 | 770.4 | 869.5 | 984.5 |
| m/z observed | n.o. | 201.1 | 272.1 | 371.2 | n.o. | 655.4* | 770.4 | 869.5 | 984.5[1] |

H-Cys — Pro — Ala — Val — Lys — Arg — Asp — Val — Asp

| | $y_{12}''$ | $y_{11}''$ | $y_{10}''$ | $y_9''$ | $y_8''$ | $y_7''$ | $y_6''$ | $y_5''$ |
|---|---|---|---|---|---|---|---|---|
| m/z expected | 1373.8 | 1276.7 | 1205.7 | 1106.6 | 978.5 | 822.4 | 707.4 | 608.3 |
| m/z observed | 1373.8*[1] | 1276.8 | 1205.7 | 1106.6 | 978.5 | n.o. | n.o. | n.o. |

| | $b_{10}$ | $b_{11}$ | $b_{12}$ |
|---|---|---|---|
| m/z expected | 1097.6 | 1244.6 | 1357.7 |
| m/z observed | 1097.6[1] | 1244.7[1] | 1357.8[1] |

—Leu — Phe — Leu — Thr-OH

| | $y_4''$ | $y_3''$ | $y_2''$ | $y_1''$ |
|---|---|---|---|---|
| m/z expected | 493.3 | 380.2 | 233.2 | 120.1 |
| m/z observed | n.o. | 380.2* | 233.2 | 120.1 |

Notes:
n.o. = Not Observed.
* = Weak Signal.
[1] = Also Observed as Doubly Charged.

SEQUENCE LISTING

<160> NUMBER OF SEQ ID NOS: 7

<210> SEQ ID NO 1
<211> LENGTH: 13

```
<212> TYPE: PRT
<213> ORGANISM: Artificial Sequence
<220> FEATURE:
<223> OTHER INFORMATION: Artificial peptide

<400> SEQUENCE: 1

Cys Pro Ala Val Lys Arg Asp Val Asp Leu Phe Leu Thr
1               5                   10

<210> SEQ ID NO 2
<211> LENGTH: 16
<212> TYPE: PRT
<213> ORGANISM: Artificial Sequence
<220> FEATURE:
<223> OTHER INFORMATION: Artificial peptide

<400> SEQUENCE: 2

Glu Gln Val Ala Gln Tyr Lys Ala Leu Pro Val Val Leu Glu Asn Ala
1               5                   10                  15

<210> SEQ ID NO 3
<211> LENGTH: 17
<212> TYPE: PRT
<213> ORGANISM: Artificial Sequence
<220> FEATURE:
<223> OTHER INFORMATION: Artificial peptide

<400> SEQUENCE: 3

Lys Ala Leu Pro Val Val Leu Glu Asn Ala Arg Ile Leu Lys Asn Cys
1               5                   10                  15

Val

<210> SEQ ID NO 4
<211> LENGTH: 17
<212> TYPE: PRT
<213> ORGANISM: Artificial Sequence
<220> FEATURE:
<223> OTHER INFORMATION: Artificial peptide

<400> SEQUENCE: 4

Arg Ile Leu Lys Asn Cys Val Asp Ala Lys Met Thr Glu Glu Asp Lys
1               5                   10                  15

Glu

<210> SEQ ID NO 5
<211> LENGTH: 16
<212> TYPE: PRT
<213> ORGANISM: Artificial Sequence
<220> FEATURE:
<223> OTHER INFORMATION: Artificial peptide

<400> SEQUENCE: 5

Lys Glu Asn Ala Leu Ser Leu Leu Asp Lys Ile Tyr Thr Ser Pro Leu
1               5                   10                  15

<210> SEQ ID NO 6
<211> LENGTH: 16
<212> TYPE: PRT
<213> ORGANISM: Artificial Sequence
<220> FEATURE:
<223> OTHER INFORMATION: Artificial peptide

<400> SEQUENCE: 6

Thr Ala Met Lys Lys Ile Gln Asp Cys Tyr Val Glu Asn Gly Leu Ile
1               5                   10                  15
```

```
<210> SEQ ID NO 7
<211> LENGTH: 16
<212> TYPE: PRT
<213> ORGANISM: Artificial Sequence
<220> FEATURE:
<223> OTHER INFORMATION: Artificial peptide

<400> SEQUENCE: 7

Ser Arg Val Leu Asp Gly Leu Val Met Thr Thr Ile Ser Ser Ser Lys
1               5                   10                  15
```

HYDROCHLORIDE SALT OF PEPTIDE AND ITS USE IN COMBINATION WITH OTHER PEPTIDES FOR IMMUNOTHERAPY

FIELD OF THE INVENTION

The present invention relates to a hydrochloride salt of a peptide and to its use in preventing or treating allergy to cats.

BACKGROUND OF THE INVENTION

The term "peptide immunotherapy" is used to describe the use of at least one peptide comprising a T cell epitope for the prevention or treatment of a disease, typically an autoimmune or an allergic disease. An example of an allergic disease is allergy to cats. Allergy to cats is typically characterised by allergic responses to one or more proteins present in cat dander, such as the protein Fel d 1.

A peptide used in peptide immunotherapy typically comprises a T cell epitope of a relevant autoantigen or allergen. Thus, for example, peptides comprising a T cell epitope of Fel d 1 are used to treat or prevent allergy to cats.

Where a peptide is to be used in peptide immunotherapy, there is a general need for it to be stable during storage and transport and to have a long shelf-life.

Background to Salt Forms of Peptides

In contrast to many low molecular drugs where the salt form can have a significant effect on their pharmaceutical, pharmacodynamic and pharmacokinetic behaviour, the various salts of peptides typically do not differ much with respect to these characteristics, are applied in the same manner and they exhibit essentially the same pharmacokinetic profile.

Most of the currently approved peptide pharmaceuticals, except for acidic or acid-labile peptides such as sincalide, are sold as acetate salts (acetates) (Vergote et al. 2009).

The first peptides used as drugs were prepared in solution and purified by counter-current distribution (CCD). CCD systems usually contain acetic acid and therefore it was logical to present the peptides purified using such systems as their acetate salts. Subsequently, when peptides were first synthesised by solid phase peptide synthesis (SPPS) in the 1980s, they were manufactured using Boc α-amino protecting group chemistry. This chemistry predicates the use of side chain protecting groups that require the use of anhydrous hydrogen fluoride for side chain deprotection and cleavage from the solid phase resin. Complete removal of residual fluoride ions from the peptides was necessary and not only was acetate a suitable molecule for replacement of the fluoride, but appropriate ion exchange resins were readily available.

With the introduction of Fmoc chemistry, side chain deprotection and cleavage from the resin could be achieved with the use of trifluoroacetic acid (TFA). The crude peptides resulting from the cleavage are typically purified by reverse phase liquid chromatography utilising elution systems that contain TFA as a modifier; following lyophilisation the purified peptides contain residual trifluoroacetate counterions. While some peptides, namely corticorelin (ovine) and Bivalirudin (Angiomax®) are available as trifluoroacetates (triflutate), ion exchange to switch the counterion to the acetate using appropriate resins is achieved readily and is usually undertaken since acetate is considered to be more acceptable from a toxicological perspective than trifluoroacetate (Hay, 2012).

The production and use of peptides as their acetate salts is advantageous for a number of reasons. Not only is acetate acceptable and compatible from a biological and toxicological perspective, but it is sufficiently volatile to allow removal of excess acetic acid during final lyophilisation of the peptide. The absolute peptide content is typically 10 to 20% higher when peptides are presented as acetates compared to when they are presented as trifluoroacetate salts due to the relative molecular weights of the two counterions. This has the potential to bring significant economic benefits although any savings gained from an increased peptide content may be offset to a degree by the costs associated with the additional ion exchange step required to convert the trifluoroacetate to the acetate form.

Due to the inherent differences in their primary sequences, there are no conditions that are universally optimum with respect to peptide stability. However, it is generally accepted that peptides typically exhibit maximal solution phase stability within the pH range 3 to 6 (Avanti, 2012), with deamidation being minimised within a pH range of 3 to 5. The use of acetate as a counterion facilitates the generation of solutions at this pH and the specific use of acetate matrices has been reported to improve the stability of peptides (Helm and Müller, 1990).

Consequently, commercially available peptides are typically produced as acetate salts unless there is a compelling reason to produce them as an alternative salt. This is confirmed, for example in Manufacturing Chemist (July/August 2012, p 40-41).

Alternative salt forms are required, or preferred, in certain circumstances, for instance, in the production of slow or controlled release preparations of peptides in biodegradable polymer formulations. WO2007/084460 (Quest Pharma) describes the preparation of salts of peptide agents using strong acids for incorporation into such formulations. The use of salts formed using strong acids relates to the neutralisation of basic functional groups contained within the peptides, i.e. at the N-terminus or within the side chains of arginine, lysine and histidine residues, through the formation of neutral salts using strong acids.

It is well recognised in the art that bioactive agents, i.e. peptides, containing basic amino functional groups interact with the biodegradable polymer and form conjugates with the polymer and/or its degradation products. These reactions can occur during preparation of the biodegradable polymer formulations, during storage thereafter and during degradation of the formulations in vivo. Neutralisation of the basic functional groups through formation of salts, such as hydrochlorides, using strong acids minimises or eliminates these reactions. Thus, the formation of salts with strong acids as described in this publication is specific to the use of peptides in biodegradable polymeric compositions.

A further example of the use of salts other than acetates is the use of HCl salts in minimising the conversion of N-terminal glutamic acid via a cyclization reaction to pyroglutamate/pyroglutamic acid (Beck et al., 2007). This particular use of non-acetate salts is specific to peptides having N-terminal glutamic acids.

Conversely, a number of disadvantages of working with strong acids are known. For instance, the use of hydrochloric acid to remove residual trifluoroacetate from peptides has been reported to result in degradation of the peptides (Andruschenko et al., 2007; Roux et al., 2008). The presence of trifluoroacetate interferes with the ability to characterize the physicochemical properties of peptides by infrared (IR) absorption spectroscopy; trifluoroacetate has a strong infrared (IR) absorption band at 1673 cm-1, significantly overlapping or even completely obscuring the amide I band of a peptide. The most convenient and widely used procedure involves lyophilizing the peptide several times in the presence of an excess of a stronger acid than trifluoroacetic acid (pKa approximately 0), i.e. generally hydrochloric acid (pKa=−7). However, this approach means working at pH<1 which can induce peptide degradation, most probably by acid hydrolysis; Andruschenko et al., (2007) reported peptide modification and reduction in thermal stability following the use of HCl to remove TFA. Interestingly, Roux et al. (2008) demonstrated the almost complete exchange of the trifluoroacetate counter-ion using acid weaker than trifluoroacetic acid, such as acetic acid (pKa=4.5) by means of an ion exchange resin as used routinely during conventional synthetic peptide manufacture, demonstrating the fact that strong acids are not required.

It is therefore currently the case that where pharmaceutically acceptable salt forms of peptides are required, it is routinely the acetate salts which are used. Stronger acids are associated with a number of potential disadvantages such as possible peptide degradation and thus are not routinely employed.

SUMMARY OF THE INVENTION

The peptide consisting of the sequence CPAVKRDVDLFLT (SEQ ID NO: 1) comprises a T cell epitope of the cat dander protein Fel d 1.

It has been determined that there are two main degradation routes for this peptide. Firstly, autocleavage of the terminal cysteine-proline residue may occur. Secondly, oxidation of the terminal cysteine residue may occur leading to cysteine sulfinic acid and dimer impurities.

It has now been found that the hydrochloride salt of the peptide consisting of the sequence of SEQ ID NO: 1 is surprisingly more stable than other salt forms of this peptide. In particular, formation of the hydrochloride salt has surprisingly been found to inhibit oxidation of the terminal cysteine residue in the peptide consisting of the sequence of SEQ ID NO: 1, thereby reducing the generation of cysteine sulfinic acid and dimer impurities. Further, formation of the hydrochloride salt has surprisingly been found to inhibit autocleavage of the terminal cysteine-proline residue in the peptide consisting of the sequence of SEQ ID NO: 1.

That the formation of the hydrochloride salt of the peptide can inhibit the above degradation pathways is a surprising finding. It is uncommon in the field of peptide pharmaceuticals to use adaptation of the salt form of the peptide to influence pharmaceutical, pharmacodynamic and pharmacokinetic behaviour. Thus, the routine adaptation of salt forms, as occurs with many low molecular weight drugs, is generally not carried out for peptide drugs. Rather, given the beneficial properties of the acetate salts in particular in relation to their pH and improved stability, acetate salts are generally used. The present inventors, however, surprisingly found that the hydrochloride salt is able to inhibit oxidation of the terminal cysteine residue.

The oxidation rate of cysteine is related directly to the ionization constant of the thiol side chain. Simple aliphatic thiols have a pKa between 7.5 and 10.5 and the ionization constant of the cysteine thiol side chains in proteins generally fall in the same range. Maintenance of the thiol group in the protonated state will minimise oxidation of cysteine residues. Although hydrochloric acid is a stronger acid than acetic acid, the pKa of acetate/acetic acid is sufficiently below that of the thiol group to maintain it in the protonated state. Thus, acetate salts will maintain the thiol group in the protonated state and there is no apparent advantage in this respect from the use of a stronger acid.

The typical means to prevent or minimise the formation of oxidation products are well known to those skilled in the art and include the removal of or minimisation of exposure to atmospheric oxygen or the addition of antioxidants, reducing agents or chelating agents (Cleland and Langer, 1994; Avanti, 2012). Antioxidants, reducing agents and chelating agents suitable for the prevention of oxidation are well known (Allen, 1999; USP34-NF29, 2011; Handbook of Pharmaceutical Excipients, 2012) and their optimal utilisation is well documented (Cleland and Langer, 1994; Avanti, 2012).

Neither hydrochloric acid nor any HCl salts formed from it have any antioxidant, reducing or chelating activity. Furthermore, hydrochloric acid and its salts are not known to prevent oxidation of peptides. Despite this, the present inventors determined that the hydrochloride salt is able to reduce oxidative degradation in the specific peptide described herein.

The present invention therefore relates to a hydrochloride salt of a peptide consisting of the sequence of CPAVKRDVDLFLT (SEQ ID NO: 1).

The invention further provides a pharmaceutical composition comprising a hydrochloride salt of a peptide consisting of the sequence of SEQ ID NO: 1 and a pharmaceutically acceptable carrier or diluent.

The invention further provides a hydrochloride salt of the invention or a pharmaceutical composition of the invention for use in a method for the prevention or treatment of allergy to cats.

The invention further provides use of a hydrochloride salt of the invention or a pharmaceutical composition of the invention in the manufacture of a medicament for the prevention or treatment of allergy to cats.

The invention further provides a method of preventing or treating allergy to cats in a subject in need thereof, the method comprising administering to the subject a therapeutically effective amount of a hydrochloride salt of the invention or a pharmaceutical composition of the invention.

DESCRIPTION OF THE DRAWINGS

FIG. 2 provides interpretation of electrospray-ionization-mass-spectrometry-collision activated dissociation-mass spectrometry (ESI-MS-CAD-MS) data obtained from the MLA01 acetate product in Example 1, and confirms that the peptide has the sequence of SEQ ID NO:1.

FIG. 4 provides interpretation of electrospray-ionization-mass-spectrometry-collision activated dissociation-mass spectrometry (ESI-MS-CAD-MS) data obtained from the MLA01 hydrochloride product in Example 1, and confirms that the peptide has the sequence of SEQ ID NO:1.

DESCRIPTION OF SEQUENCES

Figure 1:
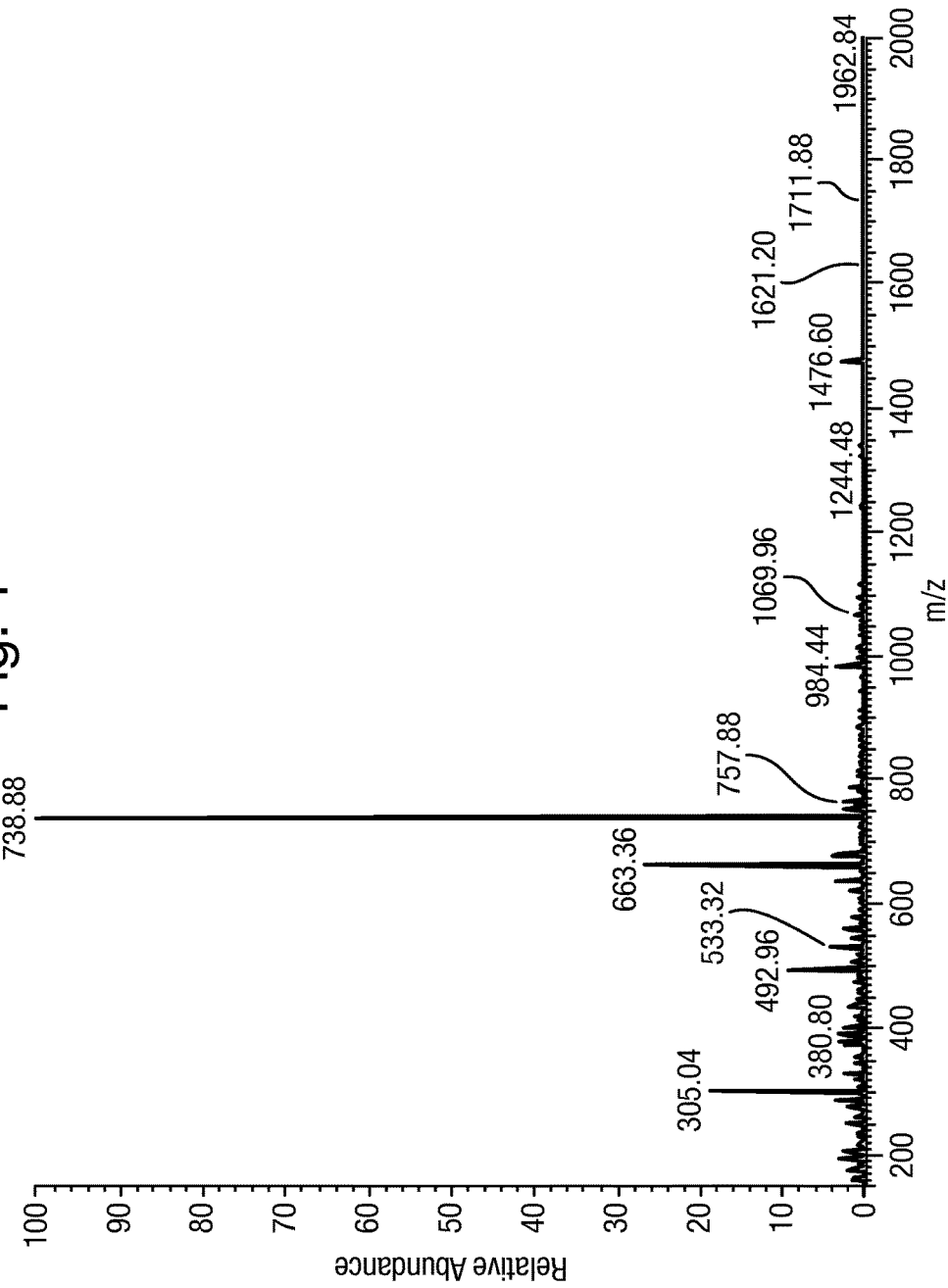
FIG. 1 shows the electrospray-ionization (ESI)-mass spectrum of the MLA01 acetate product in Example 1. There is a strong signal at m/z=738.9 corresponding to the monoisotopic $[M+2H]^{2+}$ ion of the peptide. The smaller signal at m/z=493.0 correlates with the $[M+3H]^{3+}$ ion.

SEQ ID NO: 1 to 7 provide the sequences of peptides disclosed herein. In the Examples, SEQ ID NO: 1 corresponds to peptide MLA01, SEQ ID NO: 2 corresponds to peptide MLA03, SEQ ID NO: 3 corresponds to peptide MLA04, SEQ ID NO: 4 corresponds to peptide MLA05, SEQ ID NO: 5 corresponds to peptide MLA07, SEQ ID NO: 6 corresponds to peptide MLA12 and SEQ ID NO: 7 corresponds to peptide MLA14.

DETAILED DESCRIPTION OF THE INVENTION

The invention relates to a hydrochloride salt of a peptide consisting of the sequence of:

```
                                        (SEQ ID NO: 1)
CPAVKRDVDLFLT.
```

Also disclosed herein is a peptide consisting of the sequence of any one of:

```
                                        (SEQ ID NO: 2)
EQVAQYKALPVVLENA;

(SEQ ID NO: 3)
KALPVVLENARILKNCV;

(SEQ ID NO: 4)
RILKNCVDAKMTEEDKE;

(SEQ ID NO: 5)
KENALSLLDKIYTSPL;

(SEQ ID NO: 6)
TAMKKIQDCYVENGLI;
or (SEQ ID NO: 7)
SRVLDGLVMTTISSSK,
``` or a pharmaceutically acceptable salt of any thereof.

As used herein, the term a "pharmaceutically acceptable salt" is a salt with a pharmaceutically acceptable acid or base. Pharmaceutically acceptable acids include both inorganic acids such as hydrochloric, sulphuric, phosphoric, diphosphoric, hydrobromic or nitric acid and organic acids such as citric, fumaric, maleic, malic, ascorbic, succinic, tartaric, benzoic, acetic, methanesulphonic, ethanesulphonic, benzenesulphonic or p-toluenesulphonic acid. Pharmaceutically acceptable bases include alkali metal (e.g. sodium or potassium) and alkali earth metal (e.g. calcium or magnesium) hydroxides and organic bases such as alkyl amines, aralkyl amines or heterocyclic amines. The preferred pharmaceutically acceptable salt is acetate.

The ratio of peptide to chloride in the hydrochloride salt of the invention is typically 1:1.5 to 1:7.5, preferably 1:2 to 1:4, for example about 1:3.

Typically in the hydrochloride salt of the invention one or more, preferably two or three, of (i) the N-terminal amine, (ii) the side chain of arginine, and (iii) the side chain of lysine, are protonated.

The hydrochloride salt of the invention is more stable than other salt forms of the peptide consisting of the sequence of SEQ ID NO: 1, such as acetate and trifluoroacetate. Thus, the purity of the hydrochloride salt remains higher following prolonged storage than other salt forms. Further, the levels of impurities remain lower following prolonged storage when the peptide consisting of the sequence of SEQ ID NO: 1 is in the form of a hydrochloride salt, as compared to other salt forms. In particular, formation of the hydrochloride salt inhibits autocleavage of the terminal cysteine-proline residues in the peptide consisting of the sequence of SEQ ID NO: 1. Formation of the hydrochloride salt also reduces the tendency of the terminal cysteine residue in the peptide consisting of the sequence of SEQ ID NO: 1 to oxidise, thereby inhibiting the generation of cysteine sulfinic acid and dimer impurities. As a result, the hydrochloride salt of the invention is easier to store and transport and has a longer shelf-life than other salt forms.

In a preferred aspect of the invention, therefore, the hydrochloride salt of the invention is free, or substantially free, of impurities formed by the reaction of the terminal cysteine residue.

Preferably, the hydrochloride salt is free, or substantially free, of (a) the impurity formed by cleavage of the terminal cysteine-proline residues from the peptide consisting of the sequence of SEQ ID NO: 1.

Preferably, the hydrochloride salt is free, or substantially free, of (b) the cysteine sulfinic acid form of the peptide consisting of the sequence of SEQ ID NO: 1.

Preferably, the hydrochloride salt is free, or substantially free, of (c) the dimer of the peptide consisting of the sequence of SEQ ID NO: 1.

More preferably, the hydrochloride salt is free, or substantially free, of impurities (a), (b) and (c).

A hydrochloride salt which is substantially free of a particular impurity preferably contains less than 5% by mass, more preferably less than 1% by mass, more preferably by less than 0.5% by mass, 0.1% by mass or most preferably 0.01% by mass of that particular impurity. The presence and levels of impurities (a) to (c) can be measured using any suitable technique known to those skilled in the art. High-pressure liquid chromatography (HPLC) is a preferred technique.

Pharmaceutical Compositions

The invention also relates to a pharmaceutical composition comprising a hydrochloride salt of a peptide consisting of the sequence of SEQ ID NO: 1 and a pharmaceutically acceptable carrier or diluent. Typically, the pharmaceutical composition further comprises one or more additional peptides, for example one, two, three, four, five, or six additional peptides, or pharmaceutically acceptable salts thereof.

The one or more additional peptides, for example one, two, three, four, five, or six additional peptides, or pharmaceutically acceptable salts thereof typically each comprise a T cell epitope and/or each consist of from 8 to 30 amino acids, preferably 11 to 20, for example 9, 10, 11, 12, 13, 14, 15, 16, 17, 18, 19, 20, 21, 22, 23, 24, 25, 26, 27, 28 or 29 amino acids. The T cell epitope is typically a T cell epitope of a protein present in cat dander, such as Fel d 1, Fel d 2, Fel d 4 or Fel d 7. Preferably the T cell epitope is from Fel d 1.

Preferably, the one or more additional peptides or pharmaceutically acceptable salts thereof are selected from peptides consisting of the sequences of SEQ ID NOs: 2 to 7 or pharmaceutically acceptable salts thereof.

It is preferred that the pharmaceutical composition comprises (a) a hydrochloride salt of a peptide consisting of the sequence of SEQ ID NO: 1, and (b) six additional peptides consisting of the sequences of SEQ ID NOs: 2 to 7 or pharmaceutically acceptable, preferably acetate, salts thereof, and (c) a pharmaceutically acceptable carrier or diluent.

The carrier(s) or diluent(s) must be "pharmaceutically acceptable" in the sense of being compatible with the other ingredients of the composition and not deleterious to the recipient thereof. Typically, carriers for injection, and the final composition, are sterile and pyrogen free. Preparation of a composition of the invention can be carried out using standard pharmaceutical preparation chemistries and methodologies all of which are readily available to the reasonably skilled artisan.

For example, peptides or pharmaceutically acceptable salts thereof can be combined with one or more pharmaceutically acceptable excipients or vehicles. Auxiliary substances, such as wetting or emulsifying agents, tonicity agents, pH buffering substances and the like, may be present in the excipient or vehicle. These excipients, vehicles and auxiliary substances are generally pharmaceutical agents that do not induce an immune response in the individual receiving the composition, and which may be administered without undue toxicity. Pharmaceutically acceptable excipients include, but are not limited to, liquids such as water, saline, polyethyleneglycol, hyaluronic acid, glycerol and ethanol. A thorough discussion of pharmaceutically acceptable excipients, vehicles and auxiliary substances is available in Remington's Pharmaceutical Sciences (Mack Pub. Co., N.J. 1991).

Such pharmaceutical compositions may be prepared, packaged, or sold in a form suitable for bolus administration or for continuous administration. Injectable compositions may be prepared, packaged, or sold in unit dosage form, such as in ampoules or in multi-dose containers containing a preservative. Pharmaceutical compositions include, but are not limited to, suspensions, solutions, emulsions in oily or aqueous vehicles, pastes. They may be for implantable sustained-release and/or be biodegradable. Pharmaceutical compositions may further comprise one or more additional ingredients including, but not limited to, suspending, stabilizing, or dispersing agents. In one embodiment of a composition, the active ingredient is provided in dried or freeze-dried form, e.g., as a powder or granules, for reconstitution with a suitable vehicle (e. g., sterile pyrogen-free water) prior to administration of the reconstituted composition. Pharmaceutical compositions may be prepared, packaged, or sold in the form of a sterile injectable aqueous or oily suspension or solution. This suspension or solution may be prepared according to the known art, and may comprise, in addition to the active ingredient, additional ingredients such as the dispersing agents, wetting agents, or suspending agents described herein. Such sterile injectable suspensions or solutions may be prepared using a non-toxic parenterally-acceptable diluent or solvent, such as water or 1,3-butane diol, for example. Other acceptable diluents and solvents include, but are not limited to, Ringer's solution, isotonic sodium chloride solution, and fixed oils such as synthetic mono- or di-glycerides.

Other parentally-administrable compositions which are useful include those which comprise the active ingredient in microcrystalline form, in a liposomal preparation, or as a component of a biodegradable polymer systems. Compositions for sustained release or implantation may comprise pharmaceutically acceptable polymeric or hydrophobic materials such as an emulsion, an ion exchange resin, a sparingly soluble polymer, or a sparingly soluble salt.

Alternatively, the active ingredient of a composition may be encapsulated, adsorbed to, or associated with, particulate carriers. Suitable particulate carriers include those derived from polymethyl methacrylate polymers, as well as PLG microparticles derived from poly(lactides) and poly(lactide-co-glycolides). See, e.g., Jeffery et al. (1993) Pharm. Res. 10:362-368. Other particulate systems and polymers can also be used, for example, polymers such as polylysine, polyarginine, polyornithine, spermine, spermidine, as well as conjugates of these molecules.

The preparation of any of the peptides or pharmaceutically acceptable salts thereof mentioned herein will depend upon factors such as the nature of the substance and the method of delivery. Any such substance may be administered in a variety of dosage forms. It may be administered orally (e.g. as tablets, troches, lozenges, aqueous or oily suspensions, dispersible powders or granules), parenterally, subcutaneously, by inhalation, intradermally, intravenously, intramuscularly, intrasternally, transdermally or by infusion techniques. The substance may also be administered as suppositories. A physician will be able to determine the required route of administration for each particular individual.

The compositions of the invention will comprise a suitable concentration of each peptide or salt to be effective without causing adverse reaction. Typically, the concentration of each peptide or salt in the composition will be in the range of 0.03 to 200 nmol/ml. More preferably in the range of 0.3 to 200 nmol/ml, 3 to 180 nmol/ml, 5 to 160 nmol/ml or 10 to 150 nmol/ml, for example about 100 nmol/ml.

In addition to the hydrochloride salt of a peptide consisting of the sequence of SEQ ID NO: 1, the composition of the invention preferably comprises one or more of the following:

at least one, preferably six, additional peptides or pharmaceutically acceptable salts thereof selected from the peptides consisting of the sequences of SEQ ID NOs: 2 to 7 or pharmaceutically acceptable salts thereof; and/or at least one agent to inhibit peptide dimer formation, such as thioglycerol, thioanisole or methionine; and/or at least one non-reducing carbohydrate, such as trehalose or sucrose; and optionally a substance for adjusting pH, such as phosphoric acid A particularly preferred pharmaceutical composition of the invention comprises:

a hydrochloride salt of a peptide consisting of the sequence of SEQ ID NO: 1;

acetate salts of the six peptides consisting of the sequences of SEQ ID NOs: 2 to 7;

trehalose (typically D(+) trehalose dihydrate);

thioglycerol (typically 1-thioglycerol);

methionine (typically L-methionine); and optionally phosphoric acid.

The pharmaceutical composition of the invention may be dried, preferably freeze-dried. A dried (e.g. freeze-dried) composition of the invention may be reconstituted with a suitable vehicle (e.g., sterile pyrogen-free water) prior to administration of the reconstituted composition.

The pharmaceutical composition of the invention is typically free, or substantially free, of impurities formed by reaction of the terminal cysteine residue from the peptide consisting of the sequence of SEQ ID NO: 1.

Preferably, the pharmaceutical composition is free, or substantially free, of (a) the impurity formed by cleavage of the terminal cysteine-proline residues from the peptide consisting of the sequence of SEQ ID NO: 1.

Preferably, the pharmaceutical composition is free, or substantially free, of (b) the cysteine sulfinic acid form of the peptide consisting of the sequence of SEQ ID NO: 1.

Preferably, the pharmaceutical composition is free, or substantially free, of (c) the dimer of the peptide consisting of the sequence of SEQ ID NO: 1.

More preferably, the pharmaceutical composition is free, or substantially free, of impurities (a), (b) and (c).

A pharmaceutical composition which is substantially free of a particular impurity preferably contains less than 1% by mass, more preferably less than 0.1% by mass and more preferably less than 0.01% by mass of that particular impurity. The presence and levels of impurities (a) to (c) can be measured using any suitable technique known to those skilled in the art. High-pressure liquid chromatography (HPLC) is a preferred technique.

Delivery Methods and Regimes

Once prepared the hydrochloride salt or pharmaceutical composition of the invention can be delivered to a subject in vivo using a variety of known routes and techniques. For example, a salt or composition can be provided as an injectable solution, suspension or emulsion and administered via parenteral, subcutaneous, epidermal, intradermal, intramuscular, intraarterial, intraperitoneal, intravenous injection using a conventional needle and syringe, or using a liquid jet injection system. Compositions can also be administered topically to skin or mucosal tissue, such as nasally, intratracheally, intestinal, rectally or vaginally, or provided as a finely divided spray suitable for respiratory or pulmonary administration. Other modes of administration include oral administration, suppositories, sublingual administration, and active or passive transdermal delivery techniques.

Preferred means of administration are parenteral, subcutaneous and intradermal administration. Intradermal administration is particularly preferred.

Where a peptide or salt thereof is to be administered, it is preferred to administer said peptide or salt to a site in the body where it will have the ability to contact suitable antigen presenting cells, and where it, or they, will have the opportunity to contact T cells of the individual.

Administration of a peptide, salt or composition may be by any suitable method as described above. Suitable amounts of the peptide, salt or composition may be determined empirically, but typically are in the range given below. A single administration may be sufficient to have a beneficial effect for the patient, but it will be appreciated that it may be beneficial if administration occurs more than once, in which case typical administration regimes may be, for example, once or twice a week for 2-4 weeks every 6 months, or once a day for a week every four to six months. As will be appreciated, each peptide, salt or composition may be administered to a patient singly or in combination.

Dosages for administration will depend upon a number of factors including the nature of the peptide, salt or composition, the route of administration and the schedule and timing of the administration regime. Suitable doses of a peptide or salt may be in the order of up to 10 rig, up to 15 µg, up to 20 µg, up to 25 µg, up to 30 µg, up to 35 µg, up to 50 µg, up to 100 µg, up to 500 µg or more per administration. Suitable doses may be less than 15 µg, but at least 1 ng, or at least 2 ng, or at least 5 ng, or at least 50 ng, or least 100 ng, or at least 500 ng, or at least 1 µg, or at least 10 µg. Alternatively the dose used may be higher, for example, up to 1 mg, up to 2 mg, up to 3 mg, up to 4 mg, up to 5 mg or higher. Doses may be provided in a liquid formulation, at a concentration suitable to allow an appropriate volume for administration by the selected route. It will be understood that the above doses refer to total dose in the case of a combination of peptides or salts. For example, "up to 35 µg" refers to a total peptide or salt concentration of up to 35 µg in a composition comprising a combination of more than one peptide or salt.

Preventing or Treating Allergy to Cats

The present invention provides the use of a hydrochloride salt or pharmaceutical composition of the invention for preventing or treating allergy to cats.

The hydrochloride salt or pharmaceutical composition may be administered to an individual in order to prevent allergy to cats. In this embodiment, the subject may be asymptomatic. The subject may have a genetic predisposition to the disease. A prophylactically effective amount of the hydrochloride salt or pharmaceutical composition is administered to such an individual. A prophylactically effective amount is an amount which prevents the onset of one or more symptoms of a disease or condition. A therapeutically effective amount of the hydrochloride salt or pharmaceutical composition is an amount effective to ameliorate one or more symptoms of allergy to cats. Preferably, the individual to be treated is human.

Preferably dosages, delivery methods and regimes are discussed above.

General Synthetic Procedures

Peptides can be prepared using the methods and procedures described herein, or using similar methods and procedures. It will be appreciated that where typical or preferred process conditions (i.e., reaction temperatures, times, mole ratios of reactants, solvents, pressures, etc.) are given, other process conditions can also be used unless otherwise stated. Optimum reaction conditions may vary with the particular reactants or solvent used, but such conditions can be determined by one skilled in the art by routine optimization procedures.

The peptides consisting of the sequence of SEQ ID NO: 1 to 7 can be prepared by any suitable technique.

Solid-phase peptide synthesis (SPPS) is a preferred technique. This involves formation of the peptide on small solid beads. The peptide remains covalently attached to the bead during synthesis. The peptide is synthesised using repeated cycles of coupling-washing-deprotection-washing. In particular, the free N-terminal amine of a solid-phase attached peptide is coupled to a single N-protected amino acid unit. This unit is then deprotected, revealing a new N-terminal amine to which a further protected amino acid is attached. These steps are repeated until the peptide is complete. The peptide is then cleaved from the beads using a suitable reagent.

Suitable protecting groups, reagents, solvents and reaction conditions for SPPS are well known to those skilled in the art and as such conditions can be determined by one skilled in the art by routine optimization procedures.

Pharmaceutically acceptable salts of peptides can be prepared by any suitable technique. Typically, salification involves reaction of the peptide or a salt thereof with a suitable reagent to obtain the pharmaceutically acceptable salt selected.

For example, the hydrochloride salt of the peptide consisting of the sequence of SEQ ID NO: 1 can be prepared as follows. If the peptide is initially cleaved from the solid phase using trifluoroacetic acid (TFA), then the peptide will initially be a trifluoroacetate salt. This may be further purified by any suitable technique such as high performance liquid chromatography (HPLC), e.g. using a TFA modified elutions system to produce a purified trifluoroacetate salt. The trifluoroacetate salt can then be converted into the hydrochloride salt by any known technique, such as ion exchange on a suitable column using hydrochloric acid as an eluent.

Example 1

Preparation of Salts of MLA01

Preparation of MLA01 Peptide

Synthesis was performed in a solid phase peptide synthesis (SPPS) reactor and started by suspending the substituted resin in N,N-dimethylformamide (DMF). After washing of the resin with DMF, each coupling procedure was performed by addition of the N-α-protected amino acid derivative or the N-α-protected dipeptide to the preceding amino acid in the presence of N-[(1H-Benzotriazol-1-yl)(dimethylamino)methylene]-N-methylmethanaminium tetrafluoroborate N-oxide (TBTU) and N,N-diisopropylethylamine (DIPEA) in DMF or diisopropylcarbodiimide (DIC) and 1-hydroxybenzotriazole (HOBt) in a mixture of methylene chloride (DCM) and DMF. For each single step, the solvents and/or reagents were added and the reaction mixture was stirred and subsequently filtered to remove solvents and/or reagents from the resin.

After each successful coupling or capping procedure, an Fmoc-deprotection procedure was performed. It consisted of washing of the resin with DMF, cleaving the Fmoc-group with 20% (V/V) piperidine in either DMF or 1-Methyl-2-pyrrolidone (NMP), and subsequent washings with DMF and isopropanol (IPA). For each single step, the solvents and/or reagents were added, and the reaction mixture was stirred and then filtered to remove the solvents and/or reagents from the resin.

Fmoc-deprotection and coupling procedures were repeated until the resin carries the complete peptide sequence of the corresponding MLA01 peptide. The SPPS was completed by a final Fmoc-deprotection and drying of the peptide resin under reduced pressure.

Preparation of MLA01 Trifluoroacetate

The peptide resin was treated with cold trifluoroacetic acid (TFA) at room temperature for 1.5 to 3 hours in the presence of 1,2-ethanedithiol (EDT), triisopropylsilane (TIS), and water. After filtering off and washing the resin with TFA, the product was precipitated in cold diisopropyl ether (IPE). It was then filtered off, washed with IPE, and dried under reduced pressure. The product was then reconstituted and purified by high-performance liquid chromatography (HPLC) using a TFA modified elution system.

Preparation of MLA01 Acetate

The MLA01 trifluoroacetate was reconstituted in 5% (V/V) aqueous acetic acid and loaded onto an ion exchange resin. The elution was performed with 5% (V/V) aqueous acetic acid. The MLA01 acetate may at this stage be filtered through a 0.2 μm membrane filter. The MLA01 acetate was lyophilized to yield the final product as a white to off-white powder.

The electrospray-ionization (ESI)-mass spectrum of the MLA01 acetate product shown in FIG. 1 yields a strong signal at m/z=738.9 corresponding to the monoisotopic $[M+2H]^{2+}$ ion of the peptide. The smaller signal at m/z=493.0 correlates with the $[M+3H]^{3+}$ ion. The sequence of MLA01 acetate was confirmed by electrospray-ionization-mass-spectrometry-collision activated dissociation-mass spectrometry (ESI-MS-CAD-MS) analysis, as show in FIG. 2.

Preparation of MLA01 Hydrochloride

The MLA01 trifluoroacetate was reconstituted in 0.01 M HCl in purified water and filtered where necessary. The solution was loaded onto a preparative HPLC column for ion exchange into the hydrochloride salt. The ion exchange was performed by washing the column with a 0.1 M ammonium chloride solution followed by 0.01 M HCl. The MLA01 hydrochloride may at this stage be filtered through a 0.2 μm membrane filter. Subsequently, the MLA01 hydrochloride was lyophilized to yield the final product as a white to off-white powders.

Figure 3:
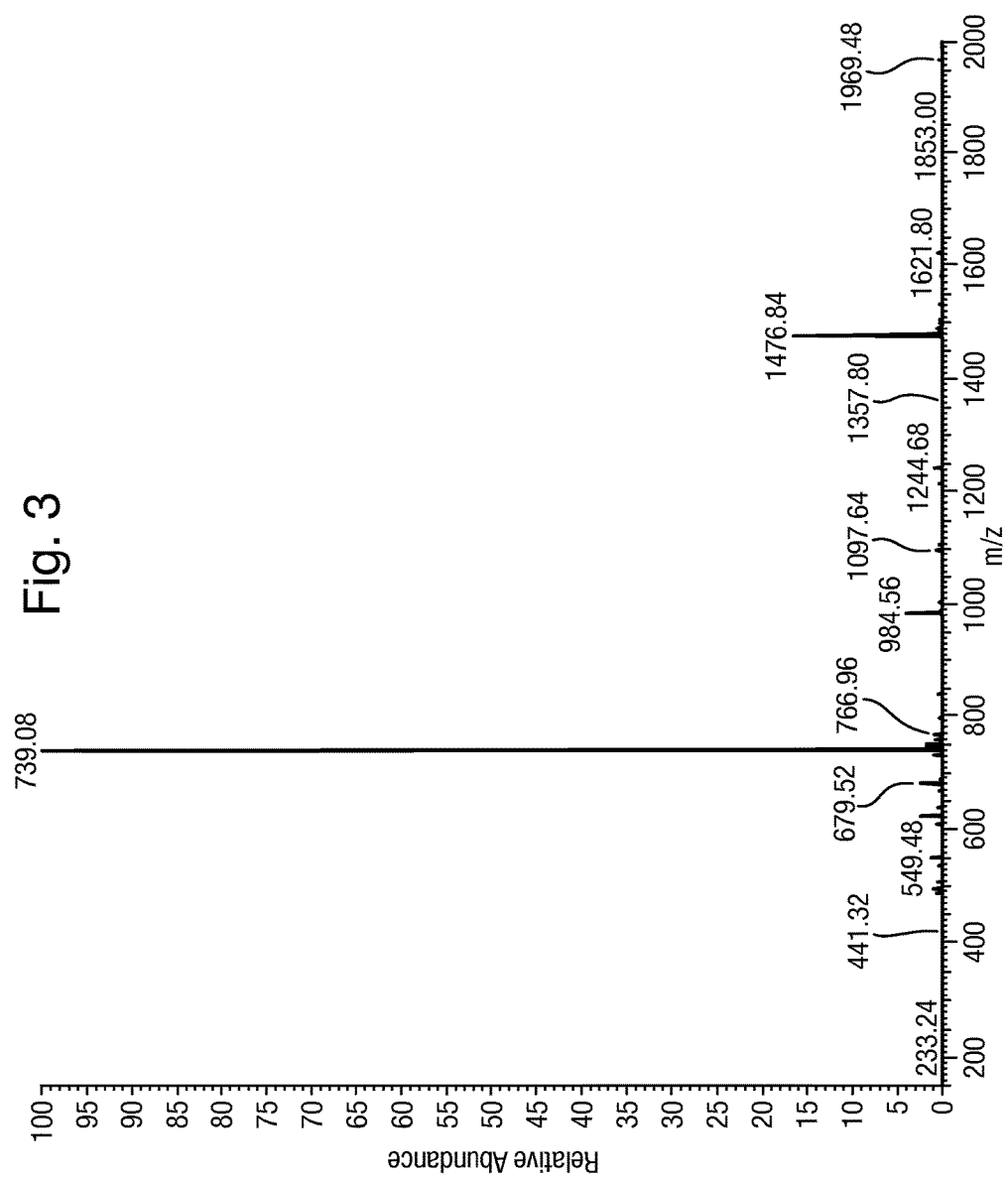
FIG. 3 shows the electrospray-ionization (ESI)-mass spectrum of the MLA01 hydrochloride product in Example 1. There are two strong signals at m/z=739.1 and 1476.8 corresponding to the monoisotopic $[M+2H]^{2+}$ and $[M+H]^{+}$ ions of the peptide, respectively.

The electrospray-ionization (ESI)-mass spectrum of the MLA01 hydrochloride product shown in FIG. 3 yields two strong signals at m/z=739.1 and 1476.8 corresponding to the monoisotopic $[M+2H]^{2+}$ and $[M+H]^{+}$ ions of the peptide, respectively. The sequence of MLA01 hydrochloride was confirmed by electrospray-ionization-mass-spectrometry-collision activated dissociation-mass spectrometry (ESI-MS-CAD-MS) analysis, as show in FIG. 4.

The chloride content of the MLA01 hydrochloride was determined by anion exchange chromatography using isocratic elution and conductivity detection with electrochemical suppression. The chloride content was calculated by means of multilevel calibration (linear regression) using sodium chloride as reference material. The chloride content of MLA01 hydrochloride was found to be between 6.1% and 6.4% by weight. This corresponds to an approximate stoichiometry of 1:3 (peptide:chloride).

Example 2

Stability of Salts of MLA01

The stability of MLA01 trifluoroacetate, MLA01 acetate and MLA01 hydrochloride when stored in an inert container over a four week period under different storage conditions was tested. The specific storage conditions evaluated are set out in Table 1.

TABLE 1

| testing condition | |
|---|---|
| Temperature/relative humidity (RH) range | Abbreviation |
| −20 ± 5° C. | −20° C. |
| 5 ± 3° C. | 5° C. |
| 25 ± 2° C., 60 ± 5% RH | 25° C./60% RH |
| 40 ± 2° C., 75 ± 5% RH | 40° C./75% RH |

Samples of each MLA01 salt were stored in inert glass containers with polypropylene twist-off caps. The samples were stored and removed at various time points for testing according to the schedule in Table 2, where X denotes removal of a sample for testing.

TABLE 2

| | testing schedule | | | |
|---|---|---|---|---|
| Weeks | −20° C. | 5° C. | 25° C./60% RH | 40° C./75% RH |
| 0 | X | — | — | — |
| 2 | X | X | X | X |
| 4 | X | X | X | X |

The purity of each sample was tested by HPLC. Purity was measured as area-percent, and the results are set out in Tables 3A to 3C below (where "—" denotes test not performed).

TABLE 3A purity of MLA01 hydrochloride

| Storage | Storage time (weeks) | | |
|---|---|---|---|
| condition | 0 | 2 | 4 |
| −20° C. | 96.6 | 94.0 | 95.6 |
| 5° C. | — | 94.0 | 95.7 |
| 25° C./60% RH | — | 94.3 | 95.5 |
| 40° C./75% RH | — | 92.4 | 95.3 |

TABLE 3B purity of MLA01 acetate

| Storage | Storage time (weeks) | | |
|---|---|---|---|
| condition | 0 | 2 | 4 |
| −20° C. | 90.6 | 84.5 | 88.1 |
| 5° C. | — | 82.7 | 84.2 |
| 25° C./60% RH | — | 75.6 | 67.2 |
| 40° C./75% RH | — | 54.0 | 39.4 |

TABLE 3C purity of MLA01 trifluoroacetate

| Storage | Storage time (weeks) | | |
|---|---|---|---|
| condition | 0 | 2 | 4 |
| −20° C. | 96.7 | 95.9 | 95.8 |
| 5° C. | — | 95.6 | 95.2 |
| 25° C./60% RH | — | 94.4 | 94.5 |
| 40° C./75% RH | — | 91.0 | 89.4 |

The levels of three specific impurities with relative retention times (RRTs) of 0.978, 1.072 and 1.099 were also measured. The impurity with an RRT of 0.978 is the impurity formed by cleavage of the terminal Cys-Pro residues from the MLA01 peptide. The impurity with an RRT of 1.072 is the cysteine sulfinic acid impurity of the MLA01 peptide. The impurity with an RRT of 1.099 is the dimer of the MLA01 peptide. The values are set out in Tables 4A to 4C below (where "<" denotes less than 0.1%).

TABLE 4A impurities in MLA01 hydrochloride

| RRT | 0 weeks, −20° C. | 4 weeks, −20° C. | 4 weeks, 40° C./ 75% RH |
|---|---|---|---|
| 0.978 | <0.1% | 0.1% | 0.2% |
| 1.072 | 0.1% | <0.1% | 0.2% |
| 1.099 | 0.34% | 0.7% | 0.6% |

TABLE 4B impurities in MLA01 acetate

| RRT | 0 weeks, −20° C. | 4 weeks, −20° C. | 4 weeks, 40° C./ 75% RH |
|---|---|---|---|
| 0.978 | 2.0% | 2.3% | 17.1% |
| 1.072 | 2.5% | 2.8% | 5.9% |
| 1.099 | 1.6% | 2.5% | 12.8% |

TABLE 4C impurities in MLA01 trifluoroacetate

| RRT | 0 weeks, −20° C. | 4 weeks, −20° C. | 4 weeks, 40° C./ 75% RH |
|---|---|---|---|
| 0.978 | <0.1% | <0.1% | 0.9% |
| 1.072 | <0.1% | <0.1% | 0.2% |
| 1.099 | 0.3% | 0.6% | 2.8% |

The stability data demonstrate that MLA01 hydrochloride is more stable than MLA01 acetate or MLA01 trifluoroacetate. In particular, the purity of MLA01 hydrochloride stayed constant over the 4 week test period. In contrast, MLA01 acetate degraded under all conditions tested and MLA01 trifluoroacetate degraded at higher temperature/humidity. These conclusions are confirmed by the levels of individual impurities over the 4 week period.

Example 3

An exemplary pharmaceutical composition of the present invention contains the components set out in Table 5. MLA03, MLA04, MLA05, MLA07, MLA12 and MLA14 acetate salts were prepared using analogous techniques to those described above in Example 1.

TABLE 5

| Raw material | Function | Nominal concentration | |
|---|---|---|---|
| MLA01, hydrochloride salt | Active ingredient | 100 µM | 147.7 µg/mL |
| MLA03, acetate salt | Active ingredient | 100 µM | 177.2 µg/mL |
| MLA04, acetate salt | Active ingredient | 100 µM | 188.0 µg/mL |
| MLA05, acetate salt | Active ingredient | 100 µM | 202.2 µg/mL |
| MLA07, acetate salt | Active ingredient | 100 µM | 180.5 µg/mL |
| MLA12, acetate salt | Active ingredient | 100 µM | 182.6 µg/mL |
| MLA14, acetate salt | Active ingredient | 100 µM | 169.4 µg/mL |
| D(+) Trehalose dihydrate | Tonicity agent | 270 mM | 102.149 mg/mL |
| 1-Thioglycerol | Reducing agent | 14 mM | 0.461 mg/mL |
| L-Methionine | Antioxidant | 5 mM | 0.746 mg/mL |
| Phosphoric acid | pH adjustment | As required | |

The composition was prepared in solution prior to being subjected to freeze-drying to produce a lyophilisate.

The invention claimed is:

1. A hydrochloride salt of a peptide consisting of the sequence of CPAVKRDVDLFLT (SEQ ID NO: 1), which is substantially free of (a) the impurity formed by cleavage of the terminal cysteine-proline residues from the peptide consisting of the sequence of SEQ ID NO: 1; and (b) the cysteine sulfinic acid form of the peptide consisting of the sequence of SEQ ID NO: 1, and (c) the dimer of the peptide consisting of the sequence of SEQ ID NO: 1.

* * * * *